(12) United States Patent
Hu

(10) Patent No.: US 9,186,121 B2
(45) Date of Patent: Nov. 17, 2015

(54) DETECTOR MODULE

(71) Applicant: Shenyang Neusoft Medical Systems Co., Ltd., Shenyang (CN)

(72) Inventor: Xiaoqing Hu, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 88 days.

(21) Appl. No.: 14/142,958

(22) Filed: Dec. 30, 2013

(65) Prior Publication Data

US 2015/0092913 A1 Apr. 2, 2015

(30) Foreign Application Priority Data

Sep. 27, 2013 (CN) .......................... 2013 1 0451458

(51) Int. Cl.
| | | |
|---|---|---|
| *G01T 1/17* | (2006.01) | |
| *A61B 6/00* | (2006.01) | |
| *G01N 23/04* | (2006.01) | |
| *G01T 1/24* | (2006.01) | |

(52) U.S. Cl.
CPC ... *A61B 6/56* (2013.01); *A61B 6/52* (2013.01); *G01N 23/046* (2013.01); *G01T 1/17* (2013.01); *G01T 1/247* (2013.01)

(58) Field of Classification Search
CPC .......... A61B 6/52; A61B 6/5205; A61B 6/56; H04N 5/32; H04N 5/321; H04N 5/335; H04N 5/369; H04N 5/3745; H04N 5/37455; H04N 5/378; H05G 1/08; H05G 1/64; G01T 1/16; G01T 1/17; G01T 1/2018; G01T 1/208; G01T 1/24; G01T 1/246; H01L 27/14658; H01L 27/14676; H01L 27/148; H01L 27/14806; H03M 1/00; H03M 1/12; G09G 2310/0264; G09G 2310/027
USPC .............. 378/19, 91, 98, 98.8, 189–192, 204, 378/210; 250/370.01, 370.08, 370.09, 250/370.14, 371, 395, 526
See application file for complete search history.

(56) References Cited

U.S. PATENT DOCUMENTS

| | | | |
|---|---|---|---|
| 4,942,400 A * | 7/1990 | Tarzaiski et al. .............. | 341/155 |
| 7,781,741 B2 * | 8/2010 | Narasimhan et al. ......... | 250/394 |
| 2011/0226951 A1 * | 9/2011 | Kammerer et al. ........ | 250/336.1 |

FOREIGN PATENT DOCUMENTS

| | | |
|---|---|---|
| CN | 1955760 A | 5/2007 |
| CN | 1969758 A | 5/2007 |
| CN | 102639061 A | 8/2012 |
| JP | 2009189384 A | 8/2009 |
| JP | 2010243394 A | 10/2010 |
| WO | 2012104775 A2 | 8/2012 |

* cited by examiner

*Primary Examiner* — Anastasia Midkiff
(74) *Attorney, Agent, or Firm* — Kilpatrick Townsend & Stockton LLP

(57) ABSTRACT

A detector module is provided, where a side of a signal adapter circuit board opposite to an X-ray source has an analog signal output terminal, at least one A/D chip is installed on an A/D conversion circuit board, and the signal adapter circuit board and the A/D conversion circuit board are connected through non-removable flexible connection with a data line. The data line is connected with the analog signal output terminal and an input terminal of the at least one A/D chip, and is adapted to transmit an analog signal. Therefore, the number of A/D conversion circuit boards in a direction of a channel of a scan chamber is increased, and a signal adapter circuit board along a direction of the channel of the scan chamber may be set to have a maximum width when detector modules are arranged closely, which is beneficial for reducing wiring density of signal wires.

12 Claims, 3 Drawing Sheets

DETECTOR MODULE

CROSS-REFERENCE TO RELATED APPLICATIONS

The present application claims priority to Chinese patent application No. 201310451458.4, filed on Sep. 27, 2013, and entitled "DETECTOR MODULE", and the entire disclosure of which is incorporated herein by reference.

FIELD OF THE DISCLOSURE

The present disclosure generally relates to medical equipment fields, and more particularly, to a detector module.

BACKGROUND OF THE DISCLOSURE

As shown in FIG. 1, in a computed tomography (CT) device, an X-ray source 101 and a detector module group 103 are installed on a rotatable gantry 104, The detector module group 103 is adapted to receive X-rays which are emitted from the X-ray source 101 and penetrates a scan chamber 102 in the CT device. Through rotation and movement of the rotatable gantry 104, CT scan of a patient in the scan chamber 102 is performed. The detector module group 103 includes a plurality of detector modules 1031 which are strongly connected. A side of each detector module 1031 which faces X-rays is installed with a detector which is adapted to receive X-rays. Another side of each detector module 1031 which is opposite to X-rays is installed with a plurality of analog signal output terminals and a plurality of analog-to-digital (A/D) chips. The plurality of analog signal output terminals are adapted to convert the received X-ray data into analog signals and output the analog signals. The plurality of A/D chips are connected with the plurality of analog signal output terminals through data lines. The plurality of A/D chips and the plurality of output terminals are installed on one circuit board and the number of the A/D chips is great, while the area of the circuit board is limited, thus, the density of electric components on the circuit board may be very high and pins' connection may be complicated, which greatly reduces the reliability of signal connection and transmission.

SUMMARY

In conventional technologies, a detector module circuit board generally has many electric components thereon, which results in a high installing density and low reliability of signal connection and transmission. Therefore, embodiments of the present disclosure provide a detector module.

In an embodiment, a detector module used in a CT device may be provided, including a signal adapter circuit board, an A/D conversion circuit board and a data line.

A side of the signal adapter circuit board which faces an X-ray source is connected with a detector array which is adapted to receive X-rays and another side of the signal adapter circuit board which is opposite to the X-ray source has an analog signal output terminal, the analog signal output terminal adapted for outputting an analog signal which is obtained by converting the X-rays received by the detector array. At least one A/D chip, which is adapted to convert the analog signal output by the analog signal output terminal into a digital signal, is installed on the A/D conversion circuit board. The signal adapter circuit board and the A/D conversion circuit board arc connected through non-removable flexible connection with a data line. The data line s connected with the analog signal output terminal and an input terminal of the at least one A/D chip, and is adapted to transmit an analog signal.

Optionally, a distance between the analog signal output terminal and a lateral edge of the signal adapter circuit board which the analog signal output terminal is towards, may be within a predetermined distance range.

Optionally, the detector module may further include a metal fixing frame, adapted to fix the signal adapter circuit board and the A/D conversion circuit board, so that the A/D conversion circuit board is located on the side of the signal adapter circuit board which is opposite to the X-ray source and an angle between the A/D conversion circuit board and the side of the signal adapter circuit board opposite to the X-ray source is within a predetermined angle range.

Optionally, the at least one A/D chip is connected with the metal fixing frame through a thermally conductive material.

Optionally, the data line may include a flexible cable.

Optionally, the detector module may include two A/D conversion circuit boards.

Optionally, a length of the data line is within a predetermined length range.

Optionally, the side of the signal adapter circuit board which faces the X-ray source being connected with the detector array which is adapted to receive X-rays may include: the side of the signal adapter circuit board which faces the X-ray source being connected with the detector array which is adapted to receive X-rays and installed on a plate through a connector.

Optionally, the detector module may further include a radiation shield layer, which is located between the signal adapter circuit board and the A/D conversion circuit board and adapted to shield the X-rays, so as to enable the A/D conversion circuit board to be in an X-ray shield region of the radiation shield layer.

Optionally, the radiation shield layer may include tungsten, tungsten alloy, lead, lead alloy, lead oxide, bismuth trioxide, gold, platinum, tantalum, or any combination thereof.

In embodiments of the present disclosure, the analog signal output terminal and the A/D chip are installed on different circuit boards respectively and connected through non-removable flexible connection with data lines, so that a working area of the detector module and space for installing the A/D chip may be enlarged. Therefore, the number of A/D conversion circuit boards in a direction of a channel of a scan chamber may be increased, and a signal adapter circuit board along a direction of the channel of the scan chamber may be set to have a maximum width when detector modules are arranged closely, which is beneficial for reducing wiring density of signal wires.

BRIEF DESCRIPTION OF THE DRAWINGS

In order to clarify the disclosure and advantages of the present disclosure, accompanying drawings used in description of embodiments of the present disclosure will be described simply. Obviously, drawings described below are only illustrative and those skilled in the art can obtain other drawings based on these drawings without creative works.

DETAILED DESCRIPTION OF THE DISCLOSURE

Embodiments of the present disclosure provide a detector module. An analog signal output terminal and an A/D chip are installed on different circuit boards respectively and connected through non-removable flexible connection with data lines, so that a working area of the detector module and space for installing the A/D chip may be enlarged, Therefore, the number of A/D conversion circuit boards in a direction of a channel of a scan chamber may be increased, and a signal adapter circuit board along a direction of the channel of the scan chamber may be set to have a maximum width when detector modules are arranged closely, which is beneficial for reducing wiring density of signal wires.

Further, the length of the data lines between input terminals of the A/D chips and the analog signal output terminals are substantially the same and as small as possible, which greatly reduces transmission noises generated when analog signals are transmitted in the data lines.

Further, a metal fixing frame is used to fix the signal adapter circuit board and the A/D conversion circuit board which are flexibly connected by the data line, which enables the A/D conversion circuit board to be located on a side of the signal adapter circuit board which is opposite to an X-ray source and to be perpendicular to the signal adapter circuit board. Thus, when a CT device is in operation, electric components, such as the A/D chip on the A/D conversion circuit board, may not be irradiated by X-rays. Besides, the A/D chip, which heats up during operation, is connected with the metal fixing frame through a material having high thermal conductivity, so that the metal fixing frame may help the A/D chip to dissipate heat.

Further, the analog signal output terminal is placed on the side of the signal adapter circuit board which is opposite to the X-ray source, near a center of the signal adapter circuit board, and towards a direction paralleled with the signal adapter circuit board. That is, the distance between the analog signal output terminal and a lateral edge of the signal adapter circuit board which the analog signal output terminal is towards may be within a predetermined distance range. Therefore, when the analog signal output terminal is connected with the input terminal of the A/D chip through the data line and a circuit board where the analog signal output terminal is located is kept being substantially perpendicular to a circuit board where the input terminal of the A/D chip is located, an adequate space may be reserved for bending the data lines without influencing normal data. transmission.

In order to clarify the objects, characteristics and advantages of the disclosure, embodiments of present disclosure will be described in detail in conjunction with accompanying drawings.

First Embodiment

Figure 1:
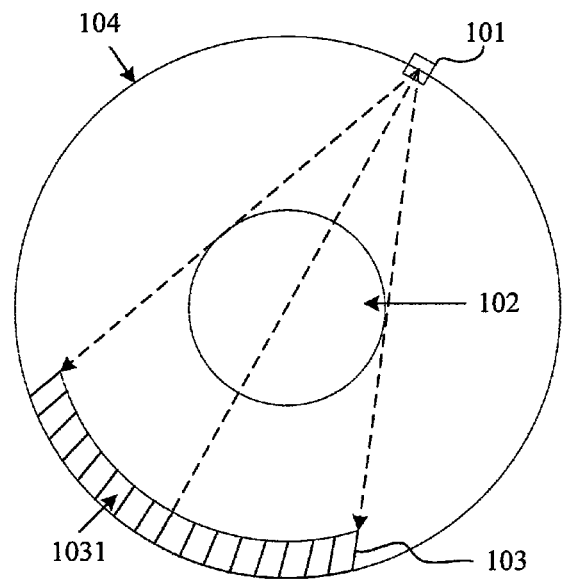
FIG. 1 schematically illustrates an internal structure diagram of a CT device.
Figure 2:
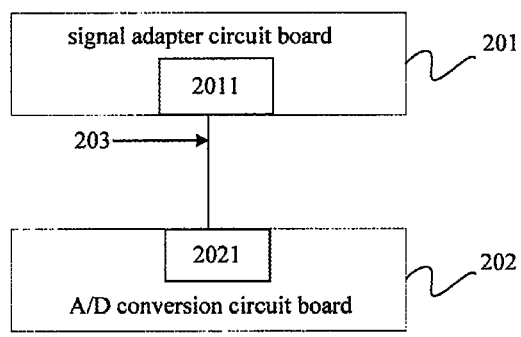
FIG. 2 schematically illustrates a block diagram of a detector module according to one embodiment of the present disclosure.

FIG. 2 schematically illustrates a block diagram of a detector module according to one embodiment of the present disclosure. The detector module includes a signal adapter circuit board 201, an A/D conversion circuit board 202 and a data line 203. Internal structures of the detector module and connections thereof are described in detail in conjunction with working principles of the detector module.

A side of the signal adapter circuit board 201 which faces an X-ray source is connected with a detector array which is adapted to receive X-rays and another side of the signal adapter circuit board 201 which is opposite to the X-ray source has an analog signal output terminal 2011, which is adapted for outputting an analog signal obtained by converting X-rays received by the detector array.

In the detector module, the signal adapter circuit board 201 is a rigid printed circuit board and adapted to convert the X-rays received by the detector array into an analog signal. Since the analog signal output terminal 2011 are disposed on the side of the signal adapter circuit board 201 which is opposite to the X-ray source, the location of the analog signal output terminal 2011 is relatively fixed and the location of the A/D chip should be adjusted.

In some embodiments, the side of the signal adapter circuit board 201 which faces the X-ray source being connected with the detector array which is adapted to receive X-rays may include: the side of the signal adapter circuit board 201 which faces the X-ray source being connected with the detector array which is adapted to receive X-rays and installed on a plate through a connector.

At least one A/D chip 2021, which is adapted to convert he analog signal output by the analog signal output terminal 2011 into a digital signal, is installed on the A/D conversion circuit board 202.

It should be noted that in embodiments of the present disclosure, the A/D chip 2021 is no longer installed on a same circuit hoard with the analog signal output terminal 2011 and the A/D conversion circuit board 202 is provided for installing the A/D chip 2021. It should be noted that, the number of A/D conversion circuit boards is not limited thereto and the number of A/D chips on each A/D conversion circuit board is not limited thereto as well. Each A/D conversion circuit board may have one or multiple A/D chips thereon, as long as all the A/D chips required in the detector module can be installed on the A/D conversion circuit boards. When there are multiple A/D chips on the A/D conversion circuit board, considering that data lines between the A/D chips and the analog signal output terminals should have a length within a predetermined length range, the multiple A/D chips may he arranged according to the distribution of the analog signal output terminals.

Besides, detectors may he increased along a direction of a channel of a scan chamber, that is, an n-by-m detector array may be formed. The signal adapter circuit board 201 coupled with a plate, may be set to have a maximum width along the direction of the channel of the scan chamber when it is flatted, which is beneficial for reducing wiring density.

Figure 3:
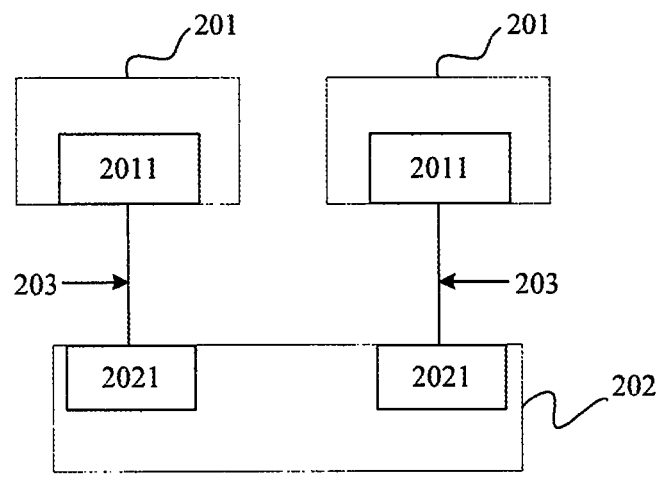
FIG. 3 schematically illustrates a block diagram of a detector module according to another embodiment of the present disclosure.

Referring to FIG. 3, in one embodiment, the detector module may include two A/D conversion circuit boards. Arrangement of the two A/D conversion circuit boards in operation will be described in a second embodiment.

The signal adapter circuit, board 201 and the two A/D conversion circuit boards 202 are connected through non-removable flexible connection with data lines 203, that is, only the data lines 203 are used to connect them. This flexible connection may he convenient for installing the signal adapter circuit board 201 and the two A/D conversion circuit boards 202 on a CT device and the non-removable connection may improve the stability of data transmission between circuit boards.

The data lines 203 are connected with the analog signal output terminals 2011 and input terminals 2021 of the two A/D chips 202, and are adapted to transmit analog signals.

In some embodiments, the data lines 203 may have a length within a predetermined length range which is not too great, and difference between the lengths of different data lines 203 may not be too great as well, so that transmission noise in the data lines 203 may be reduced. Since the data lines 203 are further adapted to connect the signal adapter circuit board 201 and the A/D conversion circuit board 202, a distance therebetween may not be too long.

In some embodiments, the analog signal output terminals 2011 are arranged on the side of the signal adapter circuit board 201 which is opposite to the X-ray source and near a center of the signal adapter circuit board 201, so that the data lines 203 may not influence the close and paratactic arrangement of detector modules. That is, a distance between the analog signal output terminals 2011 and a lateral edge of the signal adapter circuit board 201 which the analog signal output terminals 2011 are towards may be within a predetermined distance range. The predetermined distance range may be related to the material of the data lines 203, where enough space should be reserved for the data lines 203 to be bent to have an "L" shape without influencing normal data transmission.

In some embodiments, the data lines 203 may include a flexible cable.

Figure 4:
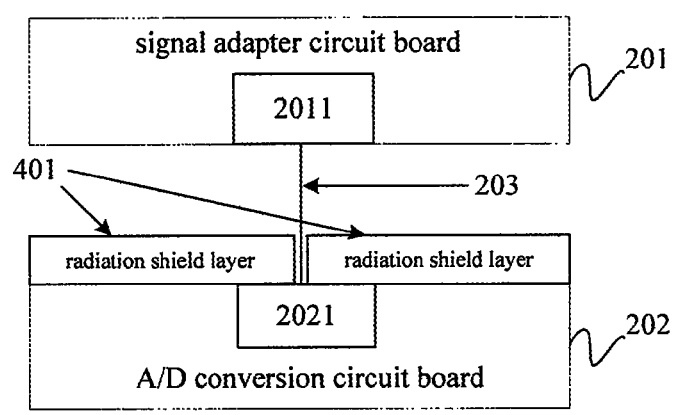
FIG. 4 schematically illustrates a block diagram of a detector module according to another embodiment of the present disclosure.

Generally, electric components installed on the A/D conversion circuit board 202 cannot operate under the radiation of X-rays since a long-time radiation of X-rays may damage internal structures of the electric components. However, the detector module operates in an environment having X-rays, thus, the detector module may further include a radiation shield part. For example, the detector module may further include a radiation shield layer 401. Referring to FIG. 4, the radiation shield layer 401 is located between the signal adapter circuit board 201 and the A/D conversion circuit board 202 and adapted to shield X-rays to enable the A/D conversion circuit board 202 to be in an X-ray shield region of the radiation shield layer 401.

In some embodiments, the radiation shield layer 401 may include tungsten, tungsten alloy, lead, lead alloy, lead oxide, bismuth trioxide, gold, platinum, tantalum, or any combination thereof.

In the above embodiments, the analog signal output terminal and the A/D chip are installed on different circuit boards respectively and connected through non-removable flexible connection with data lines, so that a working area of the detector module and space for installing the A/D chip may be enlarged. Therefore, the number of A/D conversion circuit boards in a direction of a channel of a scan chamber may be increased, and a signal adapter circuit board along a direction of the channel of the scan chamber may be set to have a maximum width when detector modules are arranged closely, which is beneficial for reducing wiring density of signal wires. Further, the length of the data line between an input terminal of each A/D chip and the analog signal output terminal is substantially the same and as small as possible, which greatly reduces transmission noises generated by the data transmission lyre transmitting an analog signal.

Further, the analog signal output, terminal is placed on the side of the signal adapter circuit board which is opposite to the X-ray source, near a center of the signal adapter circuit board, and towards a direction paralleled with the signal adapter circuit board. That is, the distance between the analog signal output terminal and a side of the signal adapter circuit board which the analog signal output terminal is towards may be within a predetermined distance range. Therefore, when the analog signal output terminal is connected with the input terminal of the A/D chip through the data line and a circuit board where the analog signal output terminal is located is kept being substantially perpendicular to a circuit board where the input terminal of the A/D chip is located, an adequate space may be reserved for bending the data lines out influencing normal data transmission.

Second Embodiment

Figure 5:
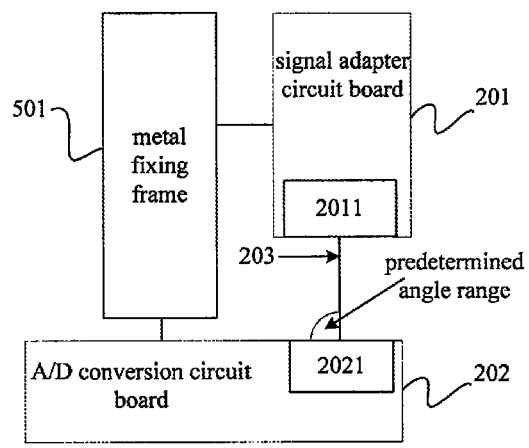
FIG. 5 schematically illustrates a block diagram of a detector module according to another embodiment of the present disclosure.

Based on the first embodiment, detailed position relations between components in the detector module when it is installed on a CT device are described hereafter. Referring to FIG. 5, FIG. 5 schematically illustrates a block diagram of a detector module according to another embodiment of the present disclosure. Internal structures of the detector module and connections thereof are described in detail in conjunction with working principles of the detector module.

The detector module further includes a metal fixing frame 501, adapted to fix the signal adapter circuit board 201 and the A/D conversion circuit board 202, so that the A/D conversion circuit board 202 is located on the side of the signal adapter circuit board 201 which is opposite to the X-ray source, and an angle between the A/D conversion circuit board 202 and the side of the signal adapter circuit board 201 opposite to the X-ray source is within a predetermined angle range.

In some embodiments, the angle may be near 90°, that is, the predetermined angle range may be from 80° to 100°. Thus, the signal adapter circuit board 201 and the A/D conversion circuit board 202 may form an "L" shape. Since detector modules need to be placed closely and paratactically, the arrangement of "L" shape may avoid interaction between adjacent detector modules, which facilitates a close and paratactic arrangement of the detector modules.

In some embodiments, the metal fixing frame 501 may further have a. good auxiliary heat dissipation function to help the A/D chip 2021 which heats up during operation to dissipate heat. In some embodiments, the A/D chip 2021 is connected with the metal fixed frame 501 through a thermally conductive material.

In some embodiments, the data line 203 may include a flexible cable.

In some embodiments, the detector module may include two A/D conversion circuit boards 202.

Figure 6:
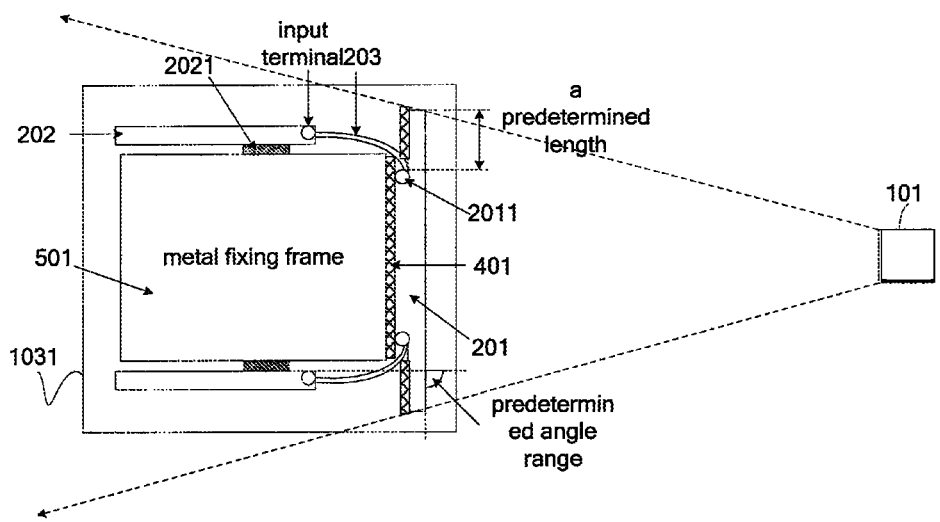
FIG. 6 schematically illustrates a cross-sectional view of a detector module according to one embodiment of the present disclosure.

For example, if the detector module has two A/D co version circuit broads 202, the two A/D conversion circuit broads 202 may be arranged opposite to each other, and the two A/D conversion circuit broads 202 and the signal adapter circuit board 201 form a "U" shape. FIG. 6 schematically illustrates a cross-sectional view of a detector module according to one embodiment of the present disclosure. In the detector module, two A/D conversion circuit broads and a signal adapter circuit board form a "U" shape, and a radiation shield layer is included. In FIG. 6, an X-ray source 101 and a detector module 1031 are shown. The detector module 1031 includes a signal adapter circuit board 201, two A/D conversion circuit broads 202, data lines 203, radiation shield layers 401 and a metal fixing frame 501.

Fixed by the metal fixing frame 501, the two A/D conversion circuit boards 202, the data lines 203 and the signal adapter circuit board 201 form a "U" shape. The data lines 203 are connected with analog signal output terminals 2011 and input terminals of A/D chips 2021. A distance between the analog signal output terminals 2011 and a lateral edge of the signal adapter circuit board 201 which the analog signal output terminal 2011 are towards may be within a predetermined distance range. An angle between each A/D conversion circuit board 202 and the signal adapter circuit board 201 is within a predetermined angle range. The A/D chips 2021 are connected with the metal fixed frame 501 through a material having high thermal conductivity, such as thermally conductive silicone. The radiation shield layers 401 are arranged on a side of the signal adapter circuit board 201 which is opposite to the X-ray source 101, so that the two A/D conversion circuit broads 202 are in an X-ray shield region formed by the radiation shield layer 401.

In the above embodiments of the present disclosure, an analog signal output terminal and an A/D chip are installed on different circuit hoards respectively and connected through non-removable flexible connection with data lines, so that a working area of the detector module and space for installing the A/D chip may be enlarged. Therefore, the number of A/D conversion circuit boards in a direction of a channel of a scan chamber may be increased, and a signal adapter circuit board along a direction of the channel of the scan chamber may be set to have a maximum width when detector modules are arranged closely, which is beneficial for reducing wiring density of signal wires. Further, the length of the data lines between input terminals of the A/D chips and the analog signal output terminals are substantially the same and as small as possible, which greatly reduces transmission noises generated when analog signals are transmitted in the data lines.

Further, a metal fixing frame is used to fix the signal adapter circuit board and the A/D conversion circuit board which are flexibly connected by the data line, which enables the A/D conversion circuit board to be located on a side of the signal adapter circuit board which is opposite to an X-ray source and to be perpendicular to the signal adapter circuit board. Thus, when a CT device is in operation, electric components, such as the A/D chip on the A/D conversion circuit board, may not be irradiated by X-rays. Besides, the A/D chip, which heats up during operation, is connected with the metal fixing frame through a material having high thermal conductivity, so that the metal fixing frame may help the A/D chip to dissipate heat.

Further, the analog signal output terminal is placed on the side of the signal adapter circuit board which is opposite to the X-ray source, near a center of the signal adapter circuit board, and towards a direction paralleled with the signal adapter circuit board. That is, the distance between the analog signal output terminal and a side of the signal adapter circuit board which the analog signal output terminal is towards may be within a predetermined distance range. Therefore, when the analog signal output terminal is connected with the input terminal of the A/D chip through the data line and a circuit board where the analog signal output terminal is located is kept being substantially perpendicular to a circuit board where the input terminal of the A/D chip is located, an adequate space may be reserved for bending the data lines without influencing normal data transmission.

It should be noted that, those skilled in the art may understand all or some of the processes in the methods described above can be realized by using computer programs to instruct corresponding hardware. The programs may be stored in a readable storage medium in a computer. When the programs are implemented, the processes in the methods in the above embodiments may be performed. The readable storage medium may be diskette, CD (Compact Disc), ROM (Read-Only Memory), RAM (Random Access Memory) or the like.

A detector module is described. Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. A detector module used in a computed tomography device, comprising:
a signal adapter circuit board, an A/D conversion circuit board and a data line,
wherein a side of the signal adapter circuit board which faces an X-ray source is connected with a detector array which is adapted to receive X-rays and another side of the signal adapter circuit board which is opposite to the X-ray source has an analog signal output terminal, the analog signal output terminal is adapted for outputting an analog signal which is obtained by converting the X-rays received by the detector array; at least one A/D chip, which is adapted to convert the analog signal output by the analog signal output terminal into a digital signal, is installed on the A/D conversion circuit board; the signal adapter circuit board and the A/D conversion circuit board are connected through non-removable flexible connection with a data line; and the data line is connected with the analog signal output terminal and an input terminal of the at least one A/D chip, and is adapted to transmit an analog signal.

2. The detector module according to claim 1, wherein a distance between the analog signal output terminal and a lateral edge of the signal adapter circuit board which the analog signal output terminal is towards, is within a predetermined distance range.

3. The detector module according to claim 1, further comprising a metal fixing frame, adapted to fix the signal adapter circuit board and the A/D conversion circuit board, so that the A/D conversion circuit board is located on the side of the signal adapter circuit board opposite to the X-ray source and an angle between the A/D conversion circuit board and the side of the signal adapter circuit board opposite to the X-ray source is within a predetermined angle range.

4. The detector module according to claim 3, wherein the at least one A/D chip is connected with the metal fixing frame through a thermally conductive material.

5. The detector module according to claim 1, wherein the data line comprises a flexible cable.

6. The detector module according to claim 3, wherein the data line comprises a flexible cable.

7. The detector module according to claim 1, wherein the detector module comprises two A/D conversion circuit boards.

8. The detector module according to claim 3, wherein the detector module comprises two A/D conversion circuit boards.

9. The detector module according to claim 1, wherein a length of the data line is within a predetermined length range.

10. The detector module according to claim 1, wherein the side of the signal adapter circuit board which faces the X-ray source being connected with the detector array which is adapted to receive X-rays comprises:
the side of the signal adapter circuit board which faces the X-ray source being connected with the detector array, wherein the detector array is adapted to receive X-rays and is installed on a plate through a connector.

11. The detector module according to claim 1, further comprising a radiation shield layer which is located between the signal adapter circuit board and the A/D conversion circuit board and adapted to shield the X-rays, so as to enable the A/D conversion circuit board to be in an X-ray shield region of the radiation shield layer.

12. The detector module according to claim 11, wherein the radiation shield layer comprises one or more of the group consisting of: tungsten, tungsten alloy, lead, lead alloy, lead oxide, bismuth trioxide, gold, platinum, tantalum, or any combination thereof.

* * * * *